(12) United States Patent
Murphy

(10) Patent No.: US 12,201,788 B2
(45) Date of Patent: Jan. 21, 2025

(54) SLOTTED MEDICAL DEVICES WITH FILLERS

(71) Applicants: STRYKER CORPORATION, Kalamazoo, MI (US); STRYKER EUROPEAN OPERATIONS LIMITED, Carrigtwohill (IE)

(72) Inventor: Murtagh M. Murphy, Cork (IE)

(73) Assignees: Stryker Corporation, Kalamazoo, MI (US); Stryker European Operations Limited, County Cork (IE)

( * ) Notice: Subject to any disclaimer, the term of this patent is extended or adjusted under 35 U.S.C. 154(b) by 0 days.

(21) Appl. No.: 17/197,568

(22) Filed: Mar. 10, 2021

(65) Prior Publication Data

US 2021/0283372 A1   Sep. 16, 2021

Related U.S. Application Data

(60) Provisional application No. 62/988,363, filed on Mar. 11, 2020.

(51) Int. Cl.
*A61M 25/01* (2006.01)
*A61L 29/14* (2006.01)
*A61M 25/09* (2006.01)

(52) U.S. Cl.
CPC ....... *A61M 25/0138* (2013.01); *A61L 29/146* (2013.01); *A61M 25/09* (2013.01)

(58) Field of Classification Search
CPC .............. A61M 25/0138; A61M 25/09; A61M 25/0051; A61M 2025/09133; A61L 29/146
See application file for complete search history.

(56) References Cited

U.S. PATENT DOCUMENTS

| 4,576,772 | A |   | 3/1986  | Carpenter |
|-----------|---|---|---------|-----------|
| 5,095,915 | A |   | 3/1992  | Engelson  |
| 5,152,744 | A | * | 10/1992 | Krause ............. A61B 17/32002 606/180 |
| 5,443,455 | A |   | 8/1995  | Hergenrother et al. |

(Continued)

FOREIGN PATENT DOCUMENTS

| EP | 1932560      | 6/2008 |
|----|--------------|--------|
| JP | H 07-051290 A | 2/1995 |

(Continued)

OTHER PUBLICATIONS

"Overview of materials for Polyether Block Amide (PEBA)", www.matweb.com/search/DataSheet.aspx?MatGUID= 57b805a667ee48f7b58b3fd8df1fa17b (accessed Dec. 22, 2022) (Year: 2022).*

(Continued)

*Primary Examiner* — Jason E Flick
*Assistant Examiner* — Adam J. Cermak
(74) *Attorney, Agent, or Firm* — Vista IP Law Group, LLP

(57) ABSTRACT

A medical device includes: an elongated member having a proximal end, a distal end, and a body extending between the proximal end and the distal end; wherein the elongated member includes a tubular section having a plurality of slots extending into a wall of the tubular section, the plurality of slots having a first slot; and wherein the elongated member further includes fillers respectively located in the slots, the fillers having a first filler, wherein the first filler has a spongy material located in the first slot.

26 Claims, 5 Drawing Sheets

(56) References Cited

U.S. PATENT DOCUMENTS

| | | | |
|---|---|---|---|
| 5,876,386 A * | 3/1999 | Samson | C08L 27/12 |
| | | | 604/524 |
| 6,004,279 A * | 12/1999 | Crowley | A61M 25/09 |
| | | | 600/585 |
| 6,024,730 A | 2/2000 | Pagan | |
| 6,488,637 B1 | 12/2002 | Eder et al. | |
| 7,878,984 B2 * | 2/2011 | Jacobsen | A61M 25/09 |
| | | | 600/585 |
| 7,989,042 B2 * | 8/2011 | Obara | A61M 25/0052 |
| | | | 600/300 |
| 9,162,040 B2 * | 10/2015 | Vo | A61M 25/0053 |
| 9,272,119 B2 * | 3/2016 | Cohen | A61M 25/0013 |
| 9,283,039 B2 * | 3/2016 | Harlan | A61B 1/0011 |
| 9,848,882 B2 * | 12/2017 | Lippert | A61B 17/12022 |
| 10,076,382 B2 * | 9/2018 | Ku | A61M 25/0138 |
| 10,265,502 B2 * | 4/2019 | Tsai | A61M 25/09 |
| 10,561,820 B2 * | 2/2020 | Sullivan | B32B 27/32 |
| 10,675,057 B2 * | 6/2020 | Krieger | A61F 2/01 |
| 10,933,226 B2 * | 3/2021 | Calhoun | A61M 25/0105 |
| 2003/0093059 A1 * | 5/2003 | Griffin | A61M 25/0045 |
| | | | 604/525 |
| 2004/0064129 A1 * | 4/2004 | Deniega | A61M 25/007 |
| | | | 604/533 |
| 2004/0181136 A1 * | 9/2004 | McDaniel | A61B 18/1492 |
| | | | 606/41 |
| 2007/0112331 A1 * | 5/2007 | Weber | A61M 25/0054 |
| | | | 604/530 |
| 2009/0043372 A1 * | 2/2009 | Northrop | A61M 25/09016 |
| | | | 623/1.15 |
| 2009/0082723 A1 * | 3/2009 | Krogh | A61B 1/00078 |
| | | | 604/95.05 |
| 2010/0256603 A1 * | 10/2010 | Lippert | A61M 25/0051 |
| | | | 604/524 |
| 2013/0046285 A1 * | 2/2013 | Griffin | A61M 25/0013 |
| | | | 604/533 |
| 2013/0296718 A1 * | 11/2013 | Ranganathan | A61M 25/09 |
| | | | 600/481 |
| 2014/0046297 A1 * | 2/2014 | Shimada | A61B 5/6852 |
| | | | 604/524 |
| 2014/0066897 A1 * | 3/2014 | Campbell | A61L 29/085 |
| | | | 604/509 |
| 2014/0257363 A1 * | 9/2014 | Lippert | A61B 17/12031 |
| | | | 606/200 |
| 2016/0066918 A1 * | 3/2016 | Chen | A61B 17/12168 |
| | | | 606/200 |
| 2016/0113713 A1 * | 4/2016 | Ku | A61M 25/0074 |
| | | | 606/41 |
| 2016/0279299 A1 * | 9/2016 | Kaplan | A61L 29/146 |
| 2017/0274179 A1 * | 9/2017 | Sullivan | B32B 27/40 |
| 2018/0071496 A1 * | 3/2018 | Snyder | A61M 25/09 |
| 2018/0369538 A1 * | 12/2018 | Lee | A61L 29/145 |
| 2019/0255290 A1 * | 8/2019 | Snyder | A61M 25/0053 |
| 2019/0381288 A1 * | 12/2019 | Mock | A61M 25/1002 |
| 2021/0106346 A1 * | 4/2021 | Wallace | A61B 17/22 |
| 2021/0268233 A1 * | 9/2021 | Bogusky | A61B 1/018 |
| 2022/0296850 A1 * | 9/2022 | Lippert | A61M 25/09 |

FOREIGN PATENT DOCUMENTS

| | | |
|---|---|---|
| JP | 2000-503225 A | 3/2000 |
| JP | 2000-197704 A | 7/2000 |
| JP | 2012-522607 A | 9/2012 |
| WO | WO 2021/183614 A1 | 9/2021 |

OTHER PUBLICATIONS

"Overview of materials for Polyetheretherketone, Unreinforced," www.matweb.com/search/DataSheet.aspx?MatGUID=2164cacabcde4391a596640d553b2ebe (accessed Jan. 9, 2023) (Year: 2022).*

PCT International Search Report and Written Opinion for International Appln. No. PCT/US2021/021653, Applicant Stryker Corporation, dated Aug. 31, 2021 (13 pages).

U.S. Appl. No. 16/676,338, filed Nov. 6, 2019, Inventor: Jeffrey Lu, Entitled: Medical Devices With Reinforced Wires.

Foreign OA for CN Patent Appln. No. 2021800172538 dated Dec. 26, 2023 (with English translation of examiner comments provided by foreign agent added at end).

Foreign Exam Report for EP Patent Appln. No. 21716882.2 dated Jan. 23, 2024.

Foreign OA for CN Patent Appln. No. 2021800172538 dated Apr. 30, 2024 (with English translated comments by the examiner).

Foreign Exam Report for EP Patent Appln. No. 21716882.2 dated Jul. 17, 2023.

Foreign Office Action for CN Patent Appln. No. 2021800172538 dated Aug. 2, 2024 (with English translation of examiner comments provided by foreign agent provided at end).

Foreign Exam Communication for EP Patent Appln. No. 21716882.2 dated Jul. 22, 2024.

Foreign Notice of Rejection for JP Patent Appln. No. 2022-552650 dated Nov. 11, 2024 (with English translation).

* cited by examiner

SLOTTED MEDICAL DEVICES WITH FILLERS

RELATED APPLICATION DATA

The present application claims priority under 35 U.S.C. § 119 to U.S. Provisional Application Ser. No. 62/988,363, filed on Mar. 11, 2020.

FIELD

The present disclosure relates generally to minimally invasive medical devices, and more specifically to minimally invasive medical devices such as maneuverable catheters, guidewires, coils and other elongated flexible members.

BACKGROUND

The use of intravascular catheters, push wires, guidewires, coils and other types of elongated delivery members for accessing and treating various types of diseases, such as vascular defects, is well-known. For example, a suitable intravascular catheter, guidewire or other delivery member may be inserted into the vascular system of a patient. Commonly used vascular application to access a target site in a patient involves inserting a guidewire through an incision in the femoral artery near the groin, and advancing the guidewire until it reaches the target site. Then, a catheter is advanced over the guidewire until an open distal end of the catheter is disposed at the target site. Simultaneously or after placement of the distal end of the catheter at the target site, an intravascular implant is advanced through the catheter via a delivery wire.

In certain applications, such as neurovascular treatment, the guidewires, delivery wires, and catheters are required to navigate tortuous and intricate vasculature. By using an appropriately sized device having the requisite performance characteristics, such as "pushability" "steerability", "torquability" and most important, distal tip flexibility, virtually any target site in the vascular system may be accessed, including that within the tortuous cerebral and peripheral vasculature. Further, the forces applied at the proximal end of these wires should be transferred to the distal ends for suitable pushability (axial rigidity) and torquability (rotation). Achieving a balance between these features is highly desirable, but difficult. For example, the guidewires and/or delivery wires may comprise variable stiffness sections (e.g., achieved by varying ratio of material, including selective reinforcement, such as braids, coils, or the like, in different sections of the wires) suitable to provide sufficient flexibility, kink resistance, pushability, and torquability to allow navigation through vasculature.

In some cases, catheters, guidewires or other delivery members may include slots along their elongated body or selected portions thereof. Incorporating slots into these elongated medical devices can modify or customize the device flexibility/stiffness. For example, distal portions of catheters, guidewires or other delivery members may have a slot pattern (e.g., more slots per area, longer slots, and/or wider slots) that increases the flexibility thereof. When used as components of a delivery system, the slotted elongated tubular devices are preferably substantially sealed (e.g., using sheath, jacket, coating or their like), in order to prevent fluid exchange (into or out of) the inner lumen of the tube, and also to enhance lubricity. Exemplary slotted and coated medical devices are disclosed in U.S. Pat. Nos. 5,095,915, 5,443,455, 6,488,637, and 9,162,040, the entire disclosures of which are incorporated by reference herein.

Having a sheath, jacket, or coating over slotted elongated tubular devices increases the volume and also the outer diameter (OD) of the device, which may negatively impact the overall performance of the device when advanced through narrow bends and tortuous vasculature.

SUMMARY

A medical device includes: an elongated member having a proximal end, a distal end, and a body extending between the proximal end and the distal end; wherein the elongated member comprises a tubular section having a plurality of openings extending into a wall of the tubular section, the plurality of openings comprising a first opening; and wherein the elongated member further comprises fillers respectively located in the openings, the filers comprising a first filler, wherein the first filler comprises a spongy material located in the first opening.

Optionally, the spongy material comprises a foam material.

Optionally, the spongy material is compressible, stretchable, or both.

Optionally, the first filler is in abutment against two opposite surfaces that define the first opening.

Optionally, the first filler is fixedly secured to the two opposite surfaces that define the first opening.

Optionally, the plurality of openings extends through the wall of the tubular section.

Optionally, the tubular section comprises a lumen defined by an inner surface of the wall of the tubular section, and wherein the first filler does not extend past the inner surface into the lumen.

Optionally, the wall of the tubular section comprises an exterior surface, and wherein
the first filler does not extend past the exterior surface.

Optionally, the first filler completely fills an entirety of the first opening.

Optionally, the first filler fills only a portion of the first opening.

Optionally, the fillers do not extend beyond boundaries of the openings.

Optionally, the spongy material comprises laser-drilled or laser-cut openings.

Optionally, the spongy material comprises a closed cell material.

Optionally, the medical device is a guidewire.
Optionally, the medical device is a delivery wire.
Optionally, the medical device is an implant.
Optionally, the medical device is a catheter.
Optionally, one of the openings has a width that is less than 0.02 inch.

A medical device includes: an elongated member having a proximal end, a distal end, and a body extending between the proximal end and the distal end; wherein the elongated member comprises a tubular section having a plurality of openings extending into a wall of the tubular section, the plurality of openings comprising a first opening; and wherein the elongated member further comprises fillers respectively located in the openings, the filers comprising a first filler that does not extend beyond any boundary of the first opening.

Optionally, the first filler comprises a spongy material located in the first opening. Optionally, the spongy material comprises a closed cell material.

Optionally, the spongy material comprises a foam material.

Optionally, the spongy material comprises laser-drilled or laser-cut openings.

Optionally, the first filler is make from a material that is compressible, stretchable, or both.

Optionally, the first filler is in abutment against two opposite surfaces that define the first opening.

Optionally, the first filler is fixedly secured to the two opposite surfaces that define the first opening.

Optionally, the plurality of openings extends through the wall of the tubular section.

Optionally, the tubular section comprises a lumen defined by an inner surface of the wall of the tubular section, and wherein the first filler does not extend past the inner surface into the lumen.

Optionally, the wall of the tubular section comprises an exterior surface, and wherein the first filler does not extend past the exterior surface.

Optionally, the first filler completely fills an entirety of the first opening.

Optionally, the first filler fills only a portion of the first opening.

Optionally, the medical device is a guidewire.

Optionally, the medical device is a delivery wire.

Optionally, the medical device is an implant.

Optionally, the medical device is a catheter.

Other and further aspects and features of embodiments will become apparent from the ensuing detailed description in view of the accompanying figures.

DETAILED DESCRIPTION

Figure 1:
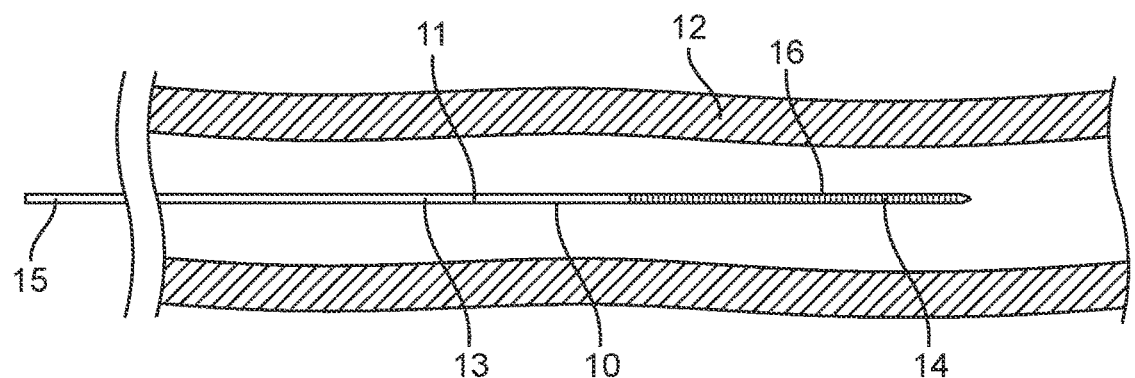
FIG. 1 illustrates a medical device.

Various embodiments are described hereinafter with reference to the figures. It should be noted that the figures are not drawn to scale and that elements of similar structures or functions are represented by the same reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure. In some cases, the term "about" may refer to a range of values that are within +/−10% of a value. For example, a value of 2 or a value of about 2 may refer to any value that is within the range of 2+/−10% (=2+/−0.2=1.8 to 2.2).

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

FIG. 1 depicts a medical device 10 according to some embodiments. The medical device 10 is configured for insertion into a blood vessel 12. The medical device 10 may be a catheter, a guidewire, a delivery wire (e.g., push wire), an implant (e.g., a coil), a combination of the foregoing, or any of other types of elongated member for medical use, such as for treatment and/or for diagnostic of a medical condition.

The medical device 10 includes an elongated member 11 having a proximal end 15, a distal end 16, and a body 13 extending between the proximal end 15 and the distal end 16. The elongated member 11 comprises a tubular section 14 at the distal end 16 of the elongated member 11. The tubular section 14 is configured to increase a flexibility of the distal end 16 of the elongated member 11. The tubular section 14 may be any elongated device or component having a lumen that can be formed from any material, such as, any suitable biocompatible metal, polymer, or a combination thereof. In some embodiments, the tubular section 14 may be a slotted hypotube. The tubular section 14 may have a circular cross-section in some embodiments. In other embodiments, the tubular section 14 of the elongated member 11 may have any cross-sectional shapes, such as an elliptical shape, or any custom-design shape. Also, in some embodiments, the tubular section 14 may have different cross-sectional shapes and/or cross-sectional dimensions along a longitudinal axis of the elongated member 11.

Figure 2A:
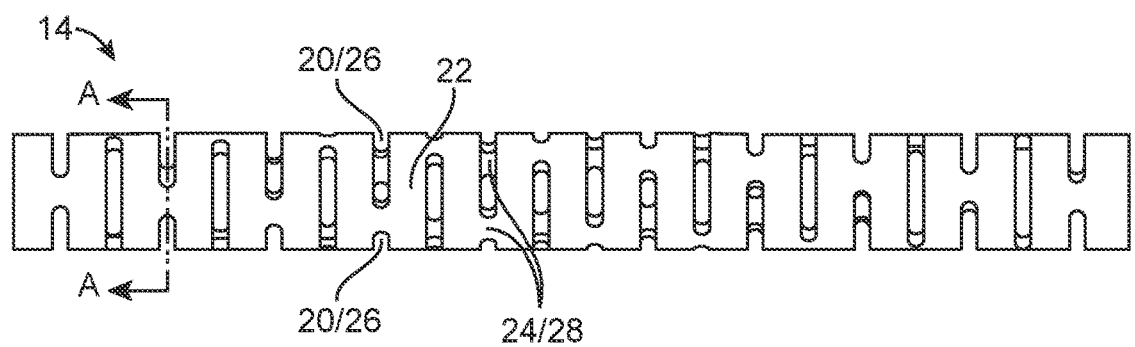
FIGS. 2A-2C illustrate the medical device of FIG. 1, particularly showing a tubular section of the medical device having a plurality of openings in the form of slots.
Figure 2B:
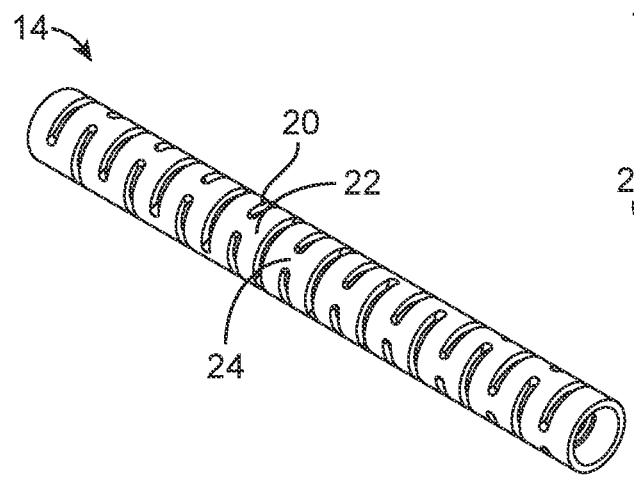
Figure 2C:
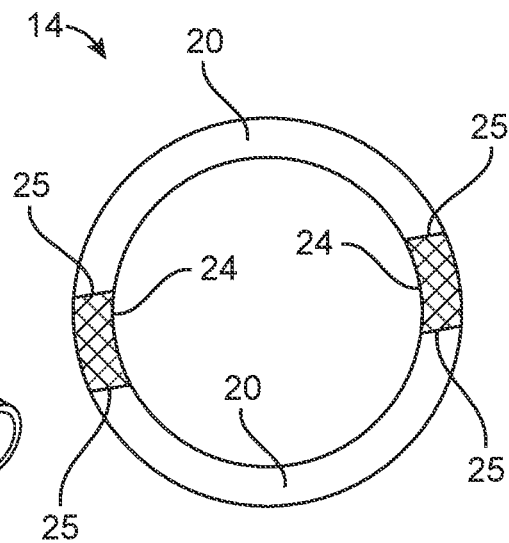

FIGS. 2A-2C depict a part of the tubular section 14. FIGS. 2A and 2B are side and perspective views, respectively. FIG. 2C is an axial cross-sectional view along the line labeled A-A in FIG. 2A. As shown in FIGS. 2A and 2B, the tubular section 14 includes a plurality of openings 20 extending into a wall of the tubular section 14. In the illustrated example, the openings 20 are elongated slots 20 that extend circumferentially around a longitudinal axis of tubular section 14. The tubular section 14 has sets 26 of slots 20 at respective longitudinal positions along the longitudinal axis of the tubular section 14 of the elongated member 11. As a result of segmentation by the slots 20, the tubular section 14 has a stack of annular segments (e.g., rings) 22 connected by a plurality of beams 24. The annular segments 22 are connected sequentially by corresponding plurality of groups (e.g., pairs) 28 of beams 24.

As shown in FIG. 2C, the beams 24 in each group 28 are disposed in the same plane that is perpendicular to the longitudinal axis of the tubular section 14. In the illustrated embodiments, each group 28 has two beams 24 disposed on opposite sides of the tubular section 14. In other embodiments, each group 28 may have more than two beams 24, or only a single beam 24. The beams 24 in each group 28 may be spaced apart from each other circumferentially by an equal distance. As shown in the figure, each beam 24 in the pair 28 has flat walls 25 at opposite ends of the beam 24. The walls 25 of the beams 24 in the pair 28 can be formed with two cuts in some embodiments.

In some embodiments, the openings (e.g., slots) 20 may be formed in the tubular section 14 by saw-cutting the tubular section 14 with circular blades, micro-machining, laser cutting, electric discharge machining, plasma arc cutting, grinding, milling, casting, molding, chemically etching, or other known suitable methods, and the like (in such cases, the removed part forming the opening 20 is a "cut-out"). In other embodiments, the tubular section with the openings 20 may be produced using "additive" manufacturing (e.g., 3D printing) rather than the various "subtractive" techniques described. In further embodiments, the tubular section with the openings 20 may be produced with casting or molding.

In some embodiments, the openings (e.g., slots) 20 extend through the wall of the tubular section 14. In particular, the openings 20 penetrate radially through the entire thickness of the wall of the tubular section 14. In such cases, the openings 20 formed in the tubular section 14 with a circular cross-section perpendicular to a longitudinal axis thereof will be arcuate when viewed from an axial direction (as shown in FIG. 2C). In other embodiments, the openings 20 do not penetrate the full thickness of the tubular section 14—i.e., the openings 20 do not penetrate completely through the wall of the tubular section 14. Instead, the openings 20 penetrate only partially into the wall of the tubular section 14. The tubular section 14 may have a wall thickness that is anywhere between 0.001 inch and 0.01 inch, or anywhere between 0.001 inch and 0.006 inch, or anywhere between 0.002 inch and 0.004 inch. In other embodiments, the tubular section 14 may have a wall thickness that is higher than 0.01 inch or less than 0.001 inch.

The openings (e.g., slots) 20 are advantageous because they enhance the flexibility of the tubular section 14 of the elongated member 11, while the beams 24 and annular segments 22 provide suitable torque transmission characteristics. The openings 20 are formed such that the annular segments 22 are interconnected by one or more beams 24. Such an interconnected structure provides a relatively high degree of torsional stiffness, while retaining a desired level of lateral bending flexibility.

It should be noted that the tubular section 14 of the elongated member 11 is not limited to having the configuration and features described in the above examples, and that the tubular section 14 may have other configurations and features in other embodiments. For example, in other embodiments, the tubular section 14 of the elongated member 11 may have different arrangements and configurations of openings 20, annular segments 22, and beams 24. In some embodiments, at least some or all of the beams 24 are disposed such that their respective longitudinal axes form a same angle or similar angles (e.g., 0 degrees+/−10 degrees) with the longitudinal axis of the tubular section 14 (like that shown in FIG. 2A). In other embodiments, the beams 24 are disposed such that their respective longitudinal axes form different angles with the longitudinal axis of the tubular section 14. It should be appreciated that the distribution and/or configuration of the openings 20, annular segments 22, and beams 24 may have any suitable variations and combinations thereof.

Additionally, the openings (e.g., slots) 20 may be arranged along the length of, or about the circumference of, the tubular section 14 in any manner to achieve desired properties. For example, adjacent openings 20, or groups of openings 20, may be arranged in a symmetrical pattern, such as being disposed essentially equally on opposite sides about the circumference of the tubular section 14. Alternatively, adjacent openings 20 or groups of openings 20 (within a plane that is perpendicular to a longitudinal axis of the tubular section 14) may be arranged in a non-symmetrical pattern. Furthermore, in some embodiments, the tubular section 14 may have only one opening (e.g., slot) 20 at each plane that is perpendicular to the longitudinal axis of the tubular section 14. The opening 20 may extend at least 45 degrees, at least 90 degrees, at least 135 degrees, at least 180 degrees, etc., circumferentially around a longitudinal axis of the tubular section 14. Additionally, adjacent openings 20, or groups of openings 20, may be equally spaced along the length of tubular section 14. Alternatively, adjacent openings 20, or groups of openings 20 may be arranged in an increasing or decreasing density pattern, and/or may be arranged in a non-symmetric or irregular pattern. Other characteristics, such as opening size, opening shape and/or opening angle with respect to the longitudinal axis of tubular section 14, may also be varied along the length of tubular section 14 in order to vary the bending flexibility/stiffness, torsional stiffness, axial stiffness, any of other structural property of the tubular section 14, or any combination of the foregoing. In further embodiments, if the openings 20 are in the form of slots, instead of having the slots extending circumferentially in a direction that is perpendicular to the longitudinal axis of the tubular section 14, the slots may extend circumferentially in a direction that is slanted (e.g., forming a non-90 degree angle) with respect to the longitudinal axis of the tubular section 14. In some embodiments, the openings 20 are implemented at a distributed fashion between ends of the tubular section 14. In other embodiments, it is contemplated that only part(s) of the tubular section 14 comprises the openings 20, and that other portions of the tubular section 14 may not include any such openings 20.

Figure 3:
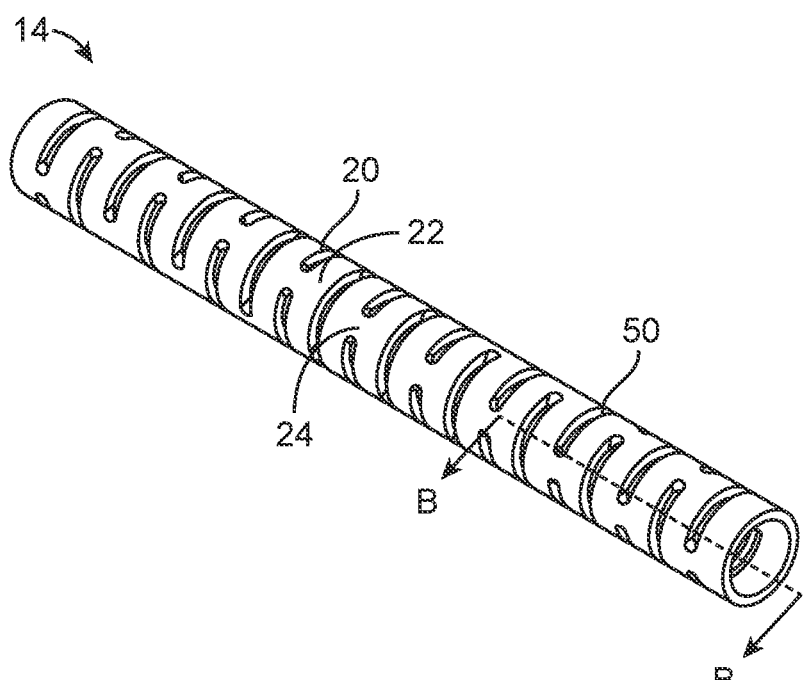
FIG. 3 illustrates the medical device of FIG. 2B, showing fillers within the slots of the tubular section of the medical device.

In one or more embodiments described herein, the elongated member 11 also includes fillers respectively located in the openings (e.g., slots) 20. FIG. 3 depicts the tubular section 14 of the elongated member 11, particularly showing the tubular section 14 having fillers 50 within respective openings 20. In the illustrated embodiments, each filler 50 comprises a spongy material. Use of the spongy material to implement the filler 50 is advantageous because it facilitates mechanical bending of the elongated member 11. Also, the spongy material may effectively lower a hardness of a bulk material, thereby enabling softness beyond the material's bulk characteristics, or enabling a more robust material to be used for manufacturing or processing purposes. The spongy material may be any porous material (e.g., microporous material) that is compressible, stretchable, or both. In one implementation, the spongy material may be a foam material. Also, in some cases, the spongy material may be achieved by laser drilling or cutting a polymer to create a sponge-like structure having openings. Holes in the sponge-like structure may not need to be sealed if the holes are sufficiently small such that blood viscosity may create an effective seal in cooperation with the holes. In some embodiments, the fillers 50 may be made from polymeric material(s), such as polyurethane, cellulose acetate, mixed esters cellulose, PTFE/polyester, acrylic copolymer, any of other biocompatible polymer, or any combination of the foregoing. The pore size of the fillers 50 may be configured to prevent viscous fluid, such as blood, outside the tubular section 14 to enter into, and to pass through, the fillers 50. If the tubular section 14 is configured to deliver a substance, the pore size of the fillers 50 may also prevent the substance from within the tubular section 14 to enter into, and to pass through, the fillers 50.

In some embodiments, the tubular section 24 of the elongated member 11 has fillers 50 in all of the respective openings 20 of the tubular section 24. In other embodiments, the fillers 50 may be disposed within just selective openings 20 (i.e., not all of the openings 20) of tubular section 14.

Figure 4:
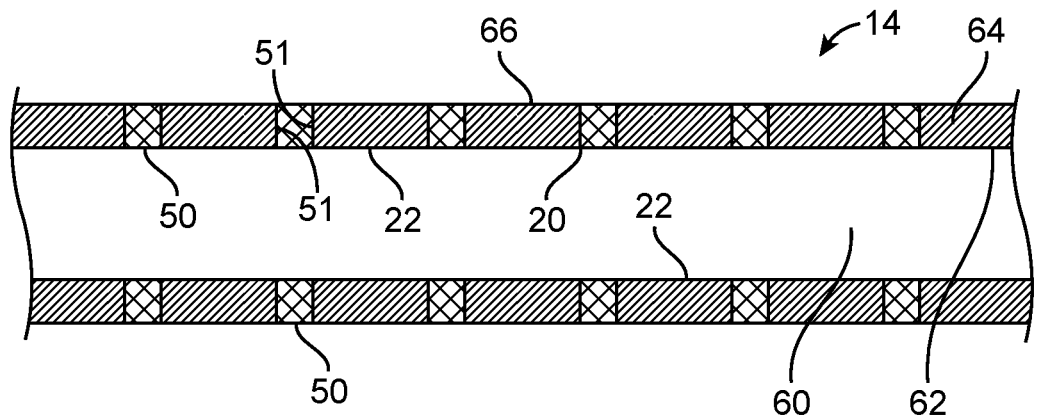
FIG. 4 illustrates a cross-section of the medical device of FIG. 3, showing fillers within the slots in a neutral configuration.

FIG. 4 illustrates a cross-sectional view along the line labeled B-B in FIG. 3 of the tubular section 14. As shown in the figure, the fillers 50 are respectfully disposed within the openings (e.g., slots) 20. When contained within the opening 20, each filler 50 is in abutment against two opposite surfaces 51 that define the opening 20. In the illustrated embodiments, each filler 50 is fixedly secured to the two opposite surfaces 51 that define the opening 20. The securing may be accomplished using an adhesive, glue, friction, etc. In some embodiments, each filler 50 completely fills an entirety of a corresponding opening 20, like that shown in FIG. 4. As shown in the figure, the filler 50 has a first filler end that is closer to the lumen 60 than to an exterior surface of the tubular section 14, and a second filler end that is closer to the exterior surface of the tubular section 14 than to the lumen 60. In other embodiments, each filler 50 fills only a portion of the opening 20.

As shown in FIG. 4, the fillers 50 do not extend beyond the boundaries of the respective openings 20. In particular, the tubular section 14 comprises a lumen 60 defined by an inner surface 62 of the wall 64 of the tubular section 14, and the fillers 50 do not extend past the inner surface 62 into the lumen 60. Also, the wall 64 of the tubular section 14 comprises an exterior surface 66, and the fillers 50 do not extend past the exterior surface 66. Thus, the fillers 50 stay between the exterior surface 66 and the inner surface 62 of the tubular section 14. This configuration is advantageous because it prevents fluid outside the tubular section 14 from entering into the lumen 60 through the openings 20, and vice versa, without requiring a layer of sealing material to be disposed on the exterior surface 66 or on the inner surface 62. Since the tubular section 14 is free of any outer jacket, coating, liner or their like, the lumen of the tubular section 14 may have a relative larger cross-sectional dimension (e.g., diameter) for a given cross-sectional dimension of the tubular section 14 to be achieved. Also, because the inner surface 62 of the tubular section 14 is free of any coating, liner, or their like, the lumen 60 of the tubular section 14 may have a relatively larger cross-sectional dimension (e.g., diameter). Having a larger lumen 60 for the tubular section 14 of the elongated member 11 is advantageous because it may allow higher volume or quantity of substance to be transported via the lumen 60. For example, neurovascular aspiration catheter may benefit from a larger diameter of the lumen 60 for aspiration of blood clots in the vasculature, than they would be otherwise when the catheter includes an outer jacket, coating, or liner at the exterior surface 66 or at the inner surface 62.

In some embodiments, the fillers 50 may be flush with the inner surface 62 of the tubular section 14, and/or the exterior surface 66 of the tubular section 14. In other embodiments, the fillers 50 may be recessed with respect to the inner surface 62 and/or the exterior surface 66 of the tubular section 14.

Figure 5:
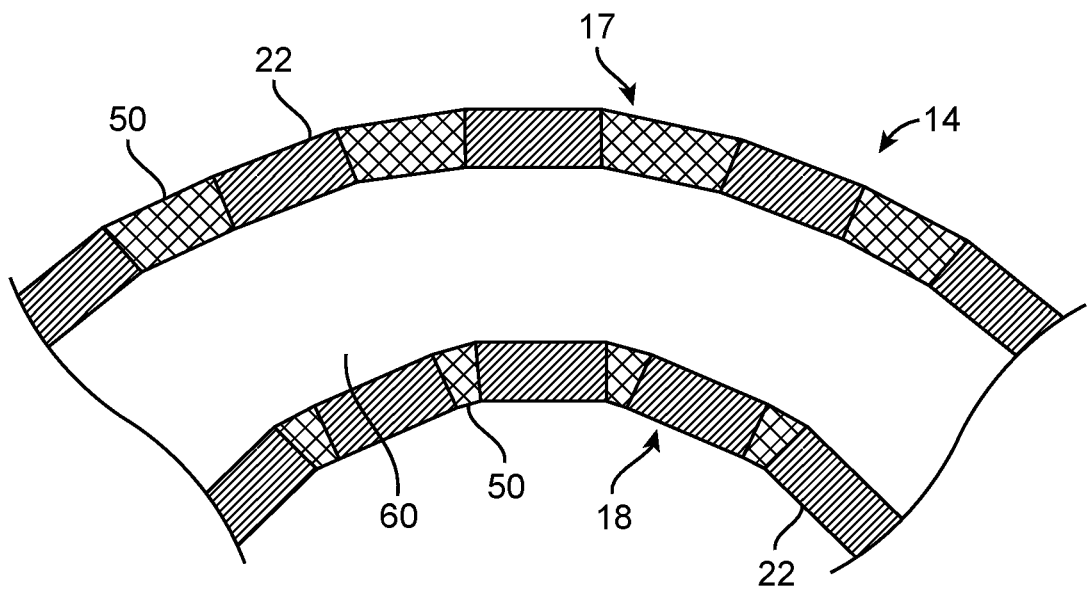
FIGS. 5 and 6 illustrate cross-sections of the medical device of FIG. 3, showing fillers within the slots in stretched and compressed configurations.
Figure 6:
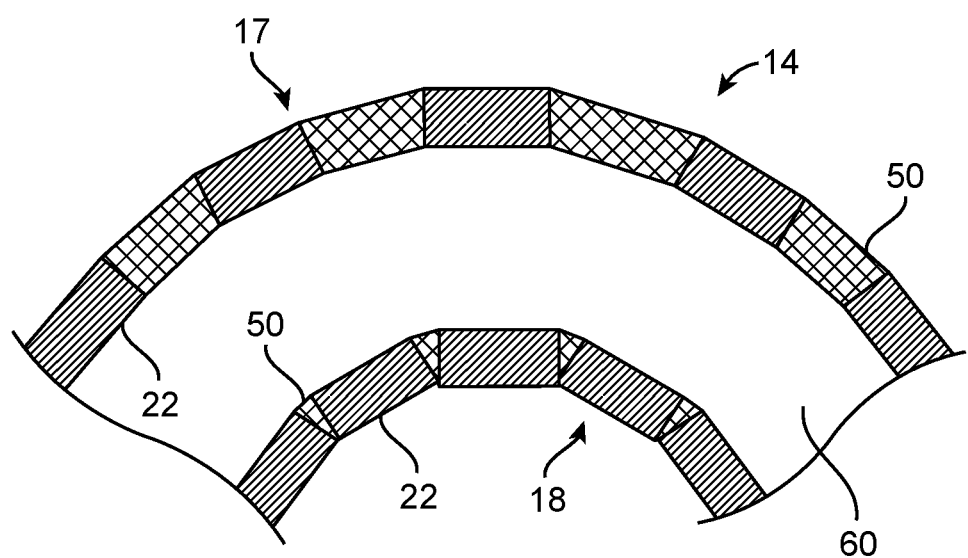

In some embodiments, the fillers 50 disposed within the openings 20 are compressible and stretchable. In some cases, a filler 50 is considered as "compressible" if it undergoes a reduction in volume under compression. As shown in FIG. 4, when the tubular section 14 is in a straight configuration, the fillers 50 are in a neutral configuration (e.g., they are not stretched or compressed). As shown in FIGS. 5 and 6, when the tubular section 14 bends, the fillers 50 on one side of the tubular section 14 are stretched due to that side of the tubular section 14 being in tension, and the fillers 50 on the opposite side of the tubular section 14 are compressed due to that side of the tubular section 14 being in compression. In particular, when the tubular section 14 bends, as shown in FIGS. 5 and 6, the tubular section 14 has a tension side 17 and a compression side 18. The fillers 50 on the tension side 17 of tubular section 14 are stretched in correspondence with an increase in the distance between adjacent annular segments 22 on the tension side 17 due to the bending of the tubular section 14. At the same time, the fillers 50 on the compression side 18 of tubular section 14 are compressed in correspondence with a decrease in the distance between adjacent annular segments 22 on the compression side 18.

In some embodiments, each filler 50 on the tension side 17 is stretchable by an amount that allows the filler 50 to remain secured to both opposite sides of the opening 20 as the two opposite sides (or surfaces 51) move apart from each other due to the bending of the tubular section 14. Each filler 50 on the compression side 18 is also compressible by an amount that allows the filler 50 to stay within the opening 20 (e.g., without being squeezed out of the opening 20) as the two opposite sides (or surfaces 51) of the opening 20 move towards each other due to the bending of the tubular section 14.

In some embodiments, each filler 50 has an uncompressed (neutral) volume, and each filler 50 is compressible to reach a compressed volume that is less than 50%, less than 40%, less than 30%, less than 20%, less than 10%, or less than 5% of the neutral volume. Also, in some embodiments, each filler 50 has an unstretched (neutral) volume, and each filler 50 is stretchable to reach a stretched volume that is more than 105%, more than 110%, more than 120%, more than 130%, more than 140%, or more than 150%, of the neutral volume. In other embodiments, each filler 50 may be compressible and/or stretchable to reach a strain (compression strain or tensile strain) that is at least 0.1, at least 0.2, at least 0.3, at least 0.4, at least 0.5, wherein a strain is defined as a change in length of the filler 50 divided by the original length of the filler 50 (e.g., strain=change in length/original length).

It should be noted that the fillers 50 are advantageous because they plug the openings 20 to prevent fluid transfer across the wall of the tubular section 14, while also allowing the tubular section 14 to be more flexible (compared to the solution in which a jacket or a coating is applied to cover the openings 20). As a result, the tubular section 14 can navigate through relatively tight bends without breaking or permanently deforming the tubular section 14. As shown in FIG.

5, the tubular section 14 may bend to form a first curvature as the tubular section 14 is moved through a blood vessel with a first bend. As shown in FIG. 6, the tubular section 14 may further bend to form a second curvature that is larger than the first curvature as the tubular section 14 is moved through a blood vessel with a tighter or sharper turn. Regardless of the curvature formed by the tubular section 14, the fillers 50 on both the tension side 17 and compression side 18 stay within the openings (e.g., slots) 20, and allow the annular segments 22 to maintain aligned with each other. As a result, an annular segment (e.g., ring) is prevented from overlapping an adjacent annular segment (e.g., ring), and/or any annular segment is prevented from moving into the lumen 60 of the tubular section 14.

Also, implementing fillers 50 using a compressible material is advantageous over using an incompressible material (i.e., material that displaces without going through volume change in response to compression). This is because openings of a slotted tube filled by incompressible material may result in a tube that is more stiff than desired, or may result in a tube having undesirable bending characteristics. In some cases, such may be compensated by attempting to cut out more materials from the tube. However, such technique may have an adverse impact on other desired properties, such as hoop strength, torque transmission capability, etc.

Various techniques may be employed to place and secure the fillers 50 in the respective openings 20. In some embodiments, the fillers 50 may be disposed within the slots 20 of the tubular section 14 by spaying or dipping the tubular section 14 in a suitable polymeric solution, allowing the solution to fill in the slots. After the solution dries or cured, it then becomes the fillers 50 within the slots 20. Any excess solution (in wet or dry form) may be removed from the tubular section 14. In other embodiments, the fillers 50 may be individually formed components that are individually inserted into the slots 20, and are individually secured to the respective slots 20, after the fillers 50 are formed.

As noted, the elongated member 11 with the tubular section 14 is not limited to the examples described. For example, in other embodiments, instead of the tubular section 14 being configured as a part of a delivery tube (e.g., catheter), the tubular section 14 may be any implant, such as a coil. In such cases, the opening 20 may be the spacing between adjacent loops of the coil. The coil may be abutted by a push wire or delivery wire, or may be detachably coupled to the push wire or the delivery wire. The coil may be configured (e.g., sized and/or shaped) to be placed in a blood vessel, and may be utilized to treat a condition inside a vasculature. For example, the coil may be used to fill a cavity of an aneurysm. In some embodiments, the filler(s) 50 is configured to be disposed within the spaces between adjacent loops of the coil. The filler(s) 50 allows the coil to navigate sharp bends while the loops of the coil stay aligned as the coil undergoes bending. Since the loops of the coil do not move transversely relatively to each other during bending of the coil, the outer surface of the coil remain substantially even. Exemplary coils for medical use are disclosed and described in U.S. patent application Ser. No. 16/676,338, the entire disclosure of which is incorporated by reference herein.

Figure 7A:
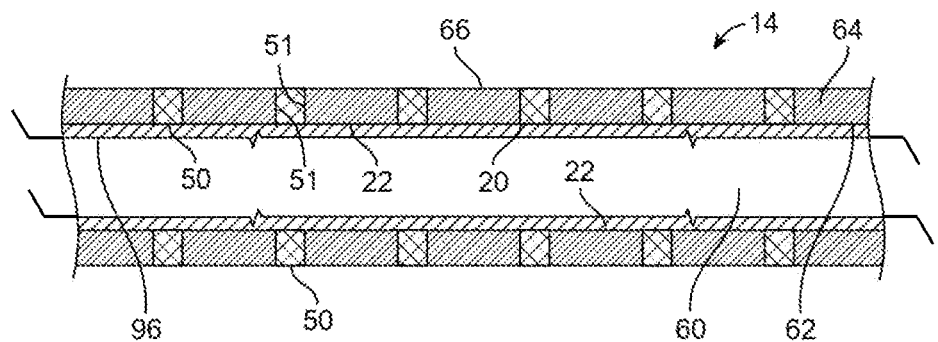
FIG. 7A illustrates the medical device of FIG. 4 having an inner layer/liner.
Figure 7B:
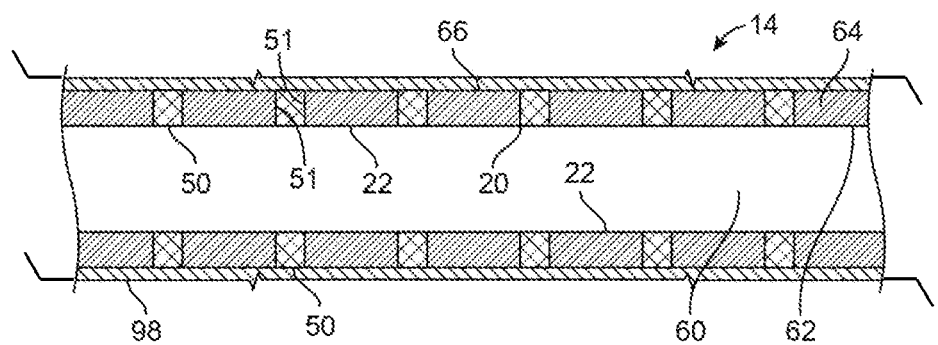
FIG. 7B illustrates the medical device of FIG. 4 having an outer layer/liner.
Figure 7C:
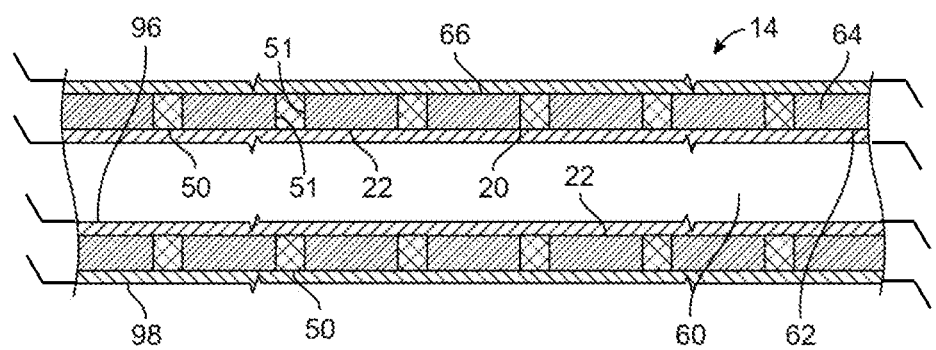
FIG. 7C illustrates the medical device of FIG. 4 having an inner layer/liner and an outer layer/liner.

Also, as described in some embodiments, the fillers 50 do not extend beyond the boundaries of the respective openings 20. However, in other embodiments, the filler 50 may extend beyond the boundary of the opening 20. For example, in other embodiments, the filler(s) 50 may extend past the inner surface of the wall of the tubular section 14 into the lumen 60, and/or does may extend past the exterior surface of the wall of the tubular section 14. In addition, in some embodiments, the part of the filler 50 extending beyond the boundaries of the opening 20 may be a bump, an elongated protrusion, a block, or may have a random shape (for example, in some cases, the part of the filler 50 extending beyond the boundary of the opening 20 may be a manufacturing artifact). Refer now to FIGS. 7A-7C, in still further embodiments, a part of the filler 50 extending past the interior surface of the tubular section 14 may extend to an inner layer 96 disposed on the interior surface of the tubular section 14, wherein the part of the filler 50 may be separately attached to the inner layer, or may be formed integrally with the inner layer 96. In further embodiments, a part of the filler 50 extending past the exterior surface of the tubular section 14 may extend to an outer layer 98 disposed on the exterior surface of the tubular section 14, wherein the part of the filler 50 may be separately attached to the outer layer 98, or may be formed integrally with the outer layer. In other embodiments, the filler 50 may have a first part extending past the exterior surface of the tubular section 14, and a second part extending past the interior surface of the tubular section 14. In such cases, the first part of the filler 50 may be separately attached to an outer layer 98 disposed on the exterior surface of the tubular section 14, and the second part of the filler 50 may be separately attached to an inner layer 96 disposed on the interior surface of the tubular section 14.

Also, in some embodiments, any of the filler(s) 50 described herein may be made from a closed cell material. In some applications, it may be desirable to use closed cell material for the filler(s) 50. For example, a catheter may be required to have certain pressure resistance, such as, for resisting aspiration (negative) pressure, and/or for injection (positive) pressure. Closed cell material is advantageous for implementing the filler(s) 50 because it does not allow a fluid leakage pathway under pressure differential. In other embodiments, the filler(s) 50 may be made from an open cell material (e.g., open cell foam). In such cases, if fluid leakage prevention is desired, an inner liner 96 and/or an outer liner (jacket) 98 may be added to the tubular structure with the fillers 50. The inner liner 96 may be a polymer inner liner in some embodiments. Also, the outer liner (jacket) 98 may also be made from a polymer in some embodiments. Alternatively, or additionally, the open cell material may have a low quantity of open cells (e.g., bubbles or cavities within the material), so that the cells (e.g., cavities) do not connect to form a pathway through a thickness of the filler 50. In some embodiments, a gassing and/or degassing process may be performed during manufacturing to achieve a certain degree of bubble and/or bubble bursting, which influences how open the cellular structure for the open cell material will be. In other embodiments, a mechanical process, such as laser cutting may be utilized to create the open cell structure.

In addition, in the embodiments in which the device 10 is a catheter, the elongated member 11 may be implemented using a tube (e.g., hypotube) with a cut pattern. In some embodiments, such cut pattern may be a laser cut pattern. Also, in some embodiments, the tube with the cut pattern may provide one or more mechanical requirements (e.g., axial stiffness, hoop strength, bending stiffness, bending radius, torsional stiffness, etc., or any combination of the foregoing) without relying on mechanical properties of the fillers 50. In some embodiments, the fillers 50 may be made from a material having an elastic modulus that is less than 10%, or less than 5%, or less than 1% or less than 0.1%, or less than 0.05%, or less than 0.01%, or less than 0.001%, of the elastic modulus of the material of the tube (implementing the elongated member 11). This allows the fillers 50 to be significantly more compressible than the material of the tube.

Using compressible material to implement the fillers 50 is advantageous because it allows the fillers 50 to not interfere with the mechanical properties of the tube. In some cases, when designing a catheter, it may be desirable to provide the proximal portion of the catheter with higher stiffness. Such may be implemented using a tube with no slots at the proximal portion. However, such a design may not meet the bending radius requirement. Accordingly, it may be desirable to add some slots to allow the proximal portion of the tube to achieve a desirable stiffness as well as the bending radius requirement. In such a design, if incompressible fillers are used to fill the slots, the bending stiffness of the catheter formed from the tube may be adversely affected, because the incompressible fillers may increase the bending stiffness of the catheter. To compensate for this, wider slots may be implemented at the tube, but widening the slots may reduce the stiffness at the proximal portion of the tube, and may also increase manufacturing cost. Use of compressible fillers 50 is advantageous because it may obviate the need to use the "wider slots" solution, while still allowing desired stiffness and bending radius to be achieved for the proximal portion of the tube (with the fillers 50).

Also, in some cases, when designing a catheter, it may be desirable to provide the distal portion of the catheter with less stiffness to achieve easier bending (compared to a proximal portion). Such may be implemented using a tube made from soft polymer. However, such a design may not meet the kink resistance requirement, and may have low hoop strength for the distal portion of the tube. Accordingly, it may be desirable to implement the distal portion of the tube using stiff hoop elements, such as metal rings/coils, metal braiding, or metal sections from cut metal tube (for achieving a desired hoop strength). The hoop elements may be spaced enough to allow the distal portion of the tube to bend with a tight bending radius (e.g., achieving 90-degree bend, 180-degree bend, or even 360-degree bend). In such a design, the wall of the tube may be thickened in order to meet column strength and tensile property requirements. However, thickening the wall of the tube may increase bending stiffness, may negatively affect the bending radius requirement, may increase the overall size of the device, and/or may reduce the lumen size of the catheter. Also, in such a design, if incompressible fillers are used to fill the slots, the bending stiffness and bending radius of the catheter may be adversely affected, because the incompressible fillers may increase the bending stiffness of the catheter, making the catheter more resistant to bending. Use of compressible fillers 50 is advantageous because it may allow desired bending stiffness, column strength, and bending radius of the tube (with the fillers 50) be achieved, while obviating the need to thicken the wall of the tube.

Furthermore, in some embodiments, the width of the openings (e.g., slots) at the elongated member 11 for accommodating the fillers 50 may have a width that is anywhere from 0.0005 inch to 0.02 inch, or anywhere from 0.0015 inch to 0.015 inch, or anywhere from 0.001 inch to 0.01 inch. Also, in some embodiments, the width of the openings (e.g., slots) at the distal end of the elongate member 11, may be different from (e.g., smaller or larger than) the width of the openings that are proximal to the distal end. For example, in some embodiments, the width of the openings accommodating the fillers 50 may be anywhere from 0.002 inch to 0.02 inch, or anywhere from 0.002 inch to 0.015 inch, or anywhere from 0.003 inch to 0.01 inch, or anywhere from 0.004 inch to 0.01 inch, at the distal end of the elongate member 11, and another portion (e.g., a proximal end) of the elongate member 11 proximal to the distal end of the elongate member 11 may have width of openings that is anywhere from 0.0005 inch to 0.002 inch, or anywhere from 0.0005 inch to 0.0015 inch, or anywhere from 0.0008 inch to 0.0012 inch (e.g., 0.001 inch).

Although particular embodiments have been shown and described, it will be understood that it is not intended to limit the claimed inventions to the preferred embodiments, and it will be obvious to those skilled in the art that various changes and modifications (e.g., the dimensions and/or shapes of various parts) may be made without department from the spirit and scope of the claimed inventions. The specification and drawings are, accordingly, to be regarded in an illustrative rather than restrictive sense. The claimed inventions are intended to cover alternatives, modifications, and equivalents.

What is claimed is:

1. A medical device, comprising:
   an elongated member having a proximal end, a distal end, and a body extending between the proximal end and the distal end;
   wherein the elongated member comprises a tubular section having a first plurality of openings and a second plurality of openings extending through an entire thickness of a wall of the tubular section, the first plurality of openings comprising a first opening;
   wherein the elongated member further comprises fillers respectively located in the openings of the first and second plurality of openings, the fillers comprising a first filler;
   wherein the first filler comprises a porous material with an elastic modulus that is less than 10% of an elastic modulus of the material of the tubular section;
   wherein the second plurality of openings are proximal to the first plurality of openings, and wherein one of the openings in the second plurality of openings has a width that is less than a width of one of the first openings in the first plurality of openings; and
   wherein the first filler is compressible to reach a compressed volume that is less than 50% of an uncompressed volume of the first filler, and/or wherein the first filler is stretchable to reach a stretched volume that is more than 120% of an unstretched volume of the first filler.

2. The medical device of claim 1, wherein the first filler comprises a closed cell material.

3. The medical device of claim 1, wherein the medical device is a guidewire, a delivery wire, a catheter or an implant.

4. The medical device of claim 1, wherein the first opening has a width that is less than 0.02 inch.

5. The medical device of claim 1, further comprising an inner layer coupled to an inner surface of the tubular section, wherein the first filler is integral with the inner layer.

6. The medical device of claim 1, further comprising an outer layer coupled to an outer surface of the tubular section.

7. The medical device of claim 6, wherein the first filler is integral with the outer layer.

8. The medical device of claim 1, wherein the first filler comprises a spongy material located in the first opening.

9. The medical device of claim 1, further comprising an outer layer coupled to an outer surface of the tubular section, and an inner layer coupled to an inner surface of the tubular section, wherein the first filler is integral with the inner layer and/or with the outer layer.

10. The medical device of claim 1, wherein the first filler is compressible and/or stretchable to reach a strain that is at least 0.5.

11. The medical device of claim 1, wherein the first plurality of openings are in a non-symmetric pattern.

12. The medical device of claim 1, wherein the first plurality of openings extend at least partly circumferentially in a slanted direction with respect to a longitudinal axis of the tubular section.

13. The medical device of claim 1, wherein the first plurality of openings comprises first slots that are non-perpendicular to a longitudinal axis of the tubular section, and wherein the second plurality of openings comprises second slots that are non-perpendicular to the longitudinal axis of the tubular section and that are proximal to the first slots.

14. The medical device of claim 1, wherein the second plurality of openings comprises at least two elongated openings.

15. The medical device of claim 1, wherein the first filler has an outer boundary defining the compressed volume of the first filler when the first filler is compressed, and defining the stretched volume of the first filler when the first filler is stretched.

16. A medical device, comprising:
an elongated member having a proximal end, a distal end, and a body extending between the proximal end and the distal end;
wherein the elongated member comprises a tubular section having a first plurality of elongated openings and a second plurality of elongated openings extending through an entire thickness of a wall of the tubular section;
wherein the elongated member further comprises fillers respectively located in the elongated openings of the first plurality of elongated openings and in the elongated openings of the second plurality of elongated openings, and wherein the fillers respectively comprise porous materials;
wherein the first plurality of elongated openings extend at least partly circumferentially in a slanted direction with respect to a longitudinal axis of the tubular section; and
wherein at least one of the fillers is compressible to reach a compressed volume that is less than 50% of an uncompressed volume of the at least one of the fillers, and/or wherein the at least one of the fillers is stretchable to reach a stretched volume that is more than 120% of an unstretched volume of the at least one of the fillers.

17. The medical device of claim 16, wherein at least one of the fillers comprises a spongy material.

18. The medical device of claim 16, wherein at least one of the fillers comprises a closed cell material.

19. The medical device of claim 16, wherein one of the fillers is compressible and/or stretchable to reach a strain that is at least 0.5.

20. The medical device of claim 16, wherein the medical device is a guidewire, a delivery wire, an implant, or a catheter.

21. The medical device of claim 16, further comprising an inner layer coupled to an inner surface of the tubular section, wherein at least one of the fillers is integral with the inner layer.

22. The medical device of claim 16, further comprising an outer layer coupled to an outer surface of the tubular section, wherein at least one of the fillers is integral with the outer surface.

23. The medical device of claim 16, wherein the second plurality of elongated openings are proximal to the first plurality of elongated openings, and wherein each of the elongated openings in the second plurality of elongated openings has a width that is less than a width of each of the elongated openings in the first plurality of elongated openings.

24. The medical device of claim 16, further comprising an outer layer coupled to an outer surface of the tubular section, and an inner layer coupled to an inner surface of the tubular section, wherein at least some of the fillers are integral with the inner layer and/or with the outer layer.

25. The medical device of claim 16, wherein at least one of the fillers has an elastic modulus that is less than 10% of an elastic modulus of a material of the tubular section.

26. The medical device of claim 16, wherein the first filler has an outer boundary defining the compressed volume of the first filler when the first filler is compressed, and defining the stretched volume of the first filler when the first filler is stretched.

* * * * *